United States Patent [19]
Moste-Deshairs et al.

[11] Patent Number: 5,741,493
[45] Date of Patent: Apr. 21, 1998

US005741493A

[54] VACCINE COMPOSITION AGAINST INFLUENZA, WITH SYNERGIC EFFECTS, CONTAINING INFLUENZA VIRUS CORE AS AN ADDITIVE

[75] Inventors: Catherine Moste-Deshairs, Ecully; Bernard Meignier, Thurins, both of France

[73] Assignee: Pasteur Merieux Serums et Vaccins, Lyons, France

[21] Appl. No.: 375,224

[22] Filed: Jan. 19, 1995

Related U.S. Application Data

[63] Continuation of Ser. No. 927,261, Nov. 22, 1992, abandoned.

[30] Foreign Application Priority Data

Jan. 24, 1991 [FR] France .................. 91 00806

[51] Int. Cl.$^6$ .............. A61K 39/00; A61K 39/145; A61K 38/00; C12N 7/00
[52] U.S. Cl. .................. 424/209.1; 424/210.1; 424/211.1; 424/184.1; 424/278.1; 514/8; 514/12; 435/235.1; 435/236; 435/238; 435/239
[58] Field of Search ............... 424/209.1, 210.1, 424/184.1, 211.1, 278.1; 435/235.1, 236, 238, 239; 514/8, 12

[56] References Cited

U.S. PATENT DOCUMENTS 4,879,213  11/1989  Fox et al. .................. 435/5

FOREIGN PATENT DOCUMENTS

| 0 041 880 | 12/1981 | European Pat. Off. . |
| WO 86/04242 | 7/1986 | WIPO . |
| WO 90/14361 | 11/1990 | WIPO . |

OTHER PUBLICATIONS

Oxford et al, 1976, Virology, 74:394–402.
Virelizier et al, 1979, British Medical Bulltein 35(1):65–68.
Ellis, R.W. "New Technologies for Making Vaccines" in *Vaccines*, Plotkin & Mortimer eds, W.B. Saunders Co. Chapter 29, pp. 568–575, 1988.
Van Regenmontal, Immunol. Today 10(8): 266–272, 1989.
Russell et al, Nature 280:147–148, 1979.
Fischer et al, Eur. J. Immunol 12:844–849, 1982.
Dawson et al, Data For Biochemical Research, 3rd ed, Clarendon Press, Oxford 1986 pp. 286–289.
Ruigrok et al, Electron Microscopy of the Influenza Virus Submembrane Structure, Virology 173:311–316, 1989.
Wraith et al, Induction of Influenza A Virus Cross–Reactive Cytotoxic T Cells by a Nucleoprotein/Haemagglutinin Preparation, J. Gen. Virol 66:1327–1331, 1985.
Kilbourne E.D., "Inactivated Influenza Vaccines" in *Vaccines*, Plotkin and Mortimer eds, W.B. Saunders Co, Chapter 19, pp. 420–434, 1988.
Maassub et al, "Live Influenza Virus Vaccine" in *Vaccines*, Plotkin and Mortimer eds., W.B. Saunders Co. Chapter 20 pp. 435–457, 1988.
R.G. Webster et al., "Potentiation of the Immune Response to Influenza Virus Subunit Vaccines," Journal of Immunology, vol. 119, No. 6, Dec. 1977, pp. 2073–2077.

*Primary Examiner*—N. M. Minnifield
*Attorney, Agent, or Firm*—Curtis Morris & Safford P.C.

[57] ABSTRACT

The use, when preparing a vaccine composition containing a standard influenza virus vaccine, of an additive which consists of a core or core fraction of at least one influenza virus, especially a fraction containing protein M; and a vaccine composition thereby obtained. The use of said additive improves the vaccine's effectiveness.

56 Claims, 2 Drawing Sheets

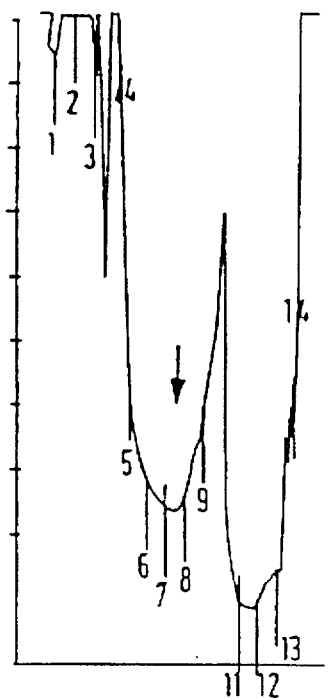
FIG.2.1a
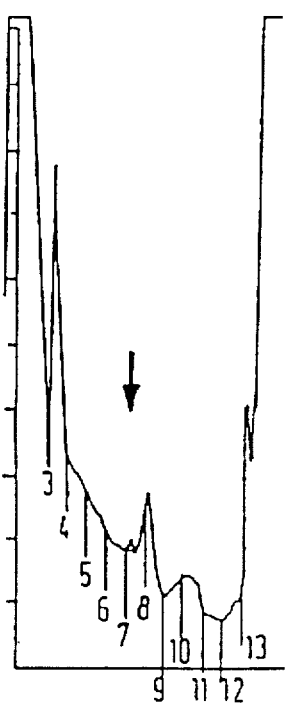
FIG.2.2a
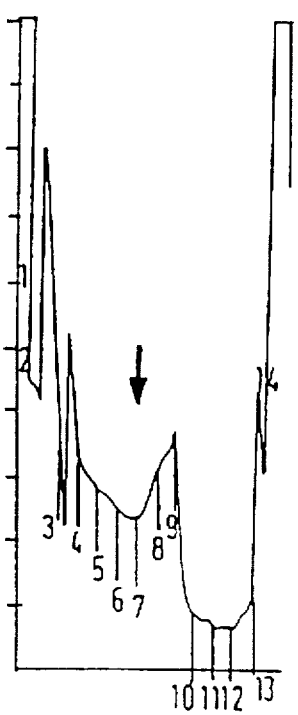
FIG.2.3a
| N° FRACTIONS | 6 | 7 | 8 | 9 | 10 |
|---|---|---|---|---|---|
| % SACCHAROSE | 31 | 35 | 38 | 42 | 45,5 |
| | 6 | 7 | 8 | 9 | 10 |
|---|---|---|---|---|---|
| | 32 | 35,5 | 39,5 | 43,5 | 47 |
| | 6 | 7 | 8 | 9 | 10 |
|---|---|---|---|---|---|
| | 33 | 36,5 | 40 | 43,5 | 47 |
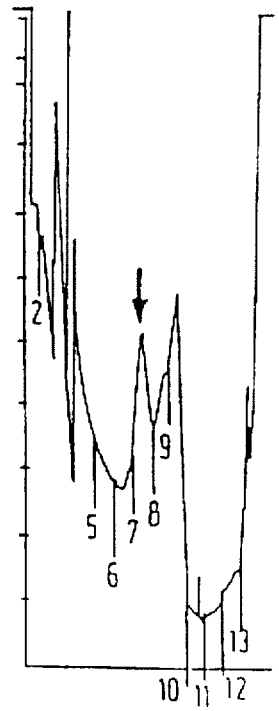
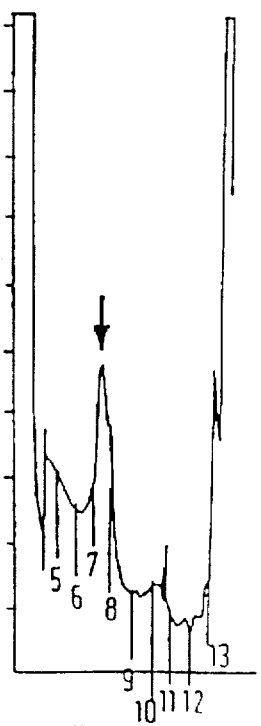
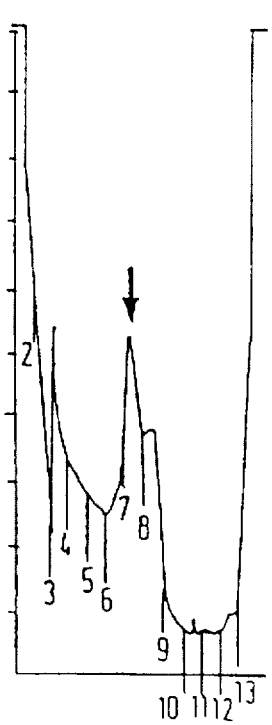
| N° FRACTIONS | 6 | 7 | 8 | 9 | 10 |
|---|---|---|---|---|---|
| % SACCHAROSE | 33 | 37 | 40,5 | 44 | 47,5 |
| | 6 | 7 | 8 | 9 | 10 |
|---|---|---|---|---|---|
| | 33 | 36 | 39,5 | 43 | 46,5 |
| | 6 | 7 | 8 | 9 | 10 |
|---|---|---|---|---|---|
| | 34 | 37 | 41 | 45 | 48 |
FIG.2.1b    FIG.2.2b    FIG.2.3b

VACCINE COMPOSITION AGAINST INFLUENZA, WITH SYNERGIC EFFECTS, CONTAINING INFLUENZA VIRUS CORE AS AN ADDITIVE

This application is a continuation of application Ser. No. 07/927,261, filed Nov. 22, 1992 now abandoned.

The object of the present invention is a vaccine composition against influenza, with synergic effects, containing influenza virus core, or a fraction thereof, as an additive to the influenza vaccine.

The influenza virus comprises a lipoprotein envelope surrounding a nucleoprotein "core". The envelope more particularly includes two glycoproteins, hemagglutinin (HA) and neuraminidase (NA). The core is a complex arrangement of viral ribonucleic acid and of several so-called "internal" proteins (polymerases, membrane protein (M) and nucleoprotein (NP)).

At present it is known that the influenza vaccine, even when correctly applied, does not completely protect all the subjects vaccinated: see for example Murphy & Webster, in 'Virology, 2ns edition (Fields et al. Ed.) 1091–1152 (1990), in particular p. 1128.

It was therefore desirable to improve the existing vaccines.

The influenza vaccines currently used are inactivated vaccines: they may be constituted of entire virions, or of virions subjected to treatment with agents which dissolve lipids ("split" vaccines), or else of purified glycoproteins ("sub-unit vaccines"). These inactivated vaccines mainly protect by causing synthesis of the receiver's antibodies directed against the hemagglutinin. It is known that antigenic evolution of the influenza virus by mutation results basically in modifications in HA and NA, while the internal proteins are only slightly modified. The result is that inactivated vaccines used at present only protect effectively as regards the strains the surface glycoproteins of which are identical or antigenically very close to those of the vaccine strains. To obtain a sufficient antigenic spectrum, the vaccines are obtained from several viral strains; they generally contain two type A strains and one type B strain. To adapt the composition of the vaccines to the antigenic evelution of the influenza viruses, the choice of strains for use in the vaccines is reviewed annually depending on the WHO or the American Food and Drug Administration recommendations, these recommendations being based on the results of international epidemiological observations. It is known that the recommended viral strains may be obtained notably from the the following organisations:

NIBSC (National Institute for Biological Standards and Control, London, UK)

WIC (World Influenza Centre, London, UK)

CDC (Centre for Disease control, Atlanta, U.S.A.)

CBER (Comity of Biological Evolution and Research, Washington, U.S.A.)

It has now been discovered that it is possible to obtain a vaccine composition with synergic effect by associating influenza virus core, or an active fraction of core, with the conventional influenza vaccine.

An active core fraction is one which, when used as an additive to a conventional vaccine, improves the effect of the vaccine.

Moreover, a protection against virus subtypes not used in the preparation of the components of the vaccine (conventional and added core or core fraction) may be obtained.

The object of the present invention, then, is a vaccine composition against influenza containing the constituents of a conventional influenza vaccine, and further containing core of at least one influenza virus strain, or a fraction of the said core, as an additive.

The conventional vaccine forming the main constituent of the vaccine composition of the invention may be an anti-influenza vaccine with complete virions, a sub-unit vaccine or a split vaccine. It may be obtained from viruses cultivated in chick embryonated eggs, or on cells.

The conventional vaccines may be prepared according to known methods, which are described by Murphy & Wzbster, op. cit., for example. Other details are given below.

Complete Virion Vaccine: this may be prepared as follows: the influenza virus, obtained by culture on chick embryonated eggs, or by culture on cells, is concentrated by ultrafiltration and then purified by zonal centrifugation or by chromatography. It is inactivated before or after purification, using formal or beta-propiolactone, for instance.

Subunit Vaccine: such a vaccine may be prepared as follows: using viral suspensions fragmented by treatment with detergent, the surface antigens (hemagglutinin, neuraminidase) are purified, by ultracentrifugation for example. The sub-unit vaccines thus contain mainly HA protein, and possible NA.

The detergent used by be cationic detergent for example, such as hexadecyl trimethyl ammonium bromide (Bachmeyer, Intervirology, 5, 260–272 (1975)), an anionic detergent such as ammonium deoxycholate (Laver & Webster, Virology 69, 511–522, 1976; Webster et al., The Journal of Immunology, Vol. 119, 2073–2077, 1977); or a nonionic detergent such as that commercialized under the name TRITON X100.

The hemagglutinin may also be isolated after treatment of the virions with a protease such as bromelain, then purified by a method such as that described by Grand and Skehel, Nature, New Biology, Vol. 238, 145–147, 1972.

Split Vaccine: It can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. A similar method to that described in French patent 2 201 079 (see more particularly example 1) can be used.

Conventional vaccines generally contain 10 to 15 µg of hemagglutinin from each of the strains entering into their composition.

The conventional influenza vaccine forming the main constituent of the vaccine composition of the invention may originate from a virus of type A, B or C, or from at least two of these three types. The same applies to the core or fraction of core.

The core or fraction of core may be prepared from viruses from the same strain as the main constituent of the composition, or from a different strain or strains, which may either be of a different type (or, for type A, a different sub-type), or, within the same type or sub-type, consist of different isolate(s) or reassortant(s).

The nomenclature of the influenza viruses and their classification into types and sub-types are described for example in WHO Bull. 58, 585–591 (1980), and in Murphy & Webster, op. cit. It is known, in particular, that human influenza virus type A includes H1N1, H2N2 and H3N2 subtypes.

In the composition of the invention, the first and second constituents, that is the conventional vaccine and the additive, may be put together in the same container. They may also be present in separate containers placed in the same wrapping, with a view to mixing them on use or administering them separately.

The composition of the invention may contain the first and second constituents, combined or separate, suspended in a suitable liquid vehicle.

The two constituents of the vaccine composition of the invention, whether together or separate, may also be presented in freeze-dried form. The liquid composition is then reconstituted by mixing with a usual liquid vehicle, at the time of using.

The composition of the invention is generally presented in the form of individual vaccine doses (unit doses), constituted either by a vaccinating-unit dose of the two constituents mixed, or by a unit dose of conventional vaccine and a unit dose of core or fraction of core.

The second constitutent of the composition of the invention (core) may be obtained according to known methods, particularly by treatment of the influenza virus using a protease such as bromelain. This treatment allows the envelope proteins to be separated from the core particles; see for example Brand & Skebel, article op. cit.

Other enzymes with analogous action to that of bromelain may be used.

The second constituent of the vaccine composition of the invention may also be composed of an active fraction of influenza virus core, this fraction being a protein or lipoprotein fraction, containing at least one active core protein (particularly M protein), or else an active fragment of this protein. The expressions "active protein" or "active fragment", or "active fraction", designate a protein or fragment of protein or core fraction capable of participating in the protection induced by the vaccine, like the core particles themselves. The active fragments may be determined by simple routine experiments, retaining those fragments which, associated with the first constituent of the vaccine composition, give better protection than that obtained with the first constituent (conventional vaccine) alone.

The core fractions, including a core protein or the fragments of the said protein, may be prepared either by virus culture and extraction, or by genetic engineering methods, or by peptidic synthesis, according to methods known per se. it should be noted that the NP protein is not an active core fraction, as defined above. The combination M+NP constitutes an active fraction which is about as active as the M protein contained therein.

The second constituent (additive) of the vaccine of the invention is particularly M protein, or membrane protein, sometimes called matrix protein. Two matrix proteins play a role in the assembly of the virus when it replicates: M1 protein, which belongs to the virus structure, and M2 protein, which has been detected in the complete virus but a considerable proportion of which is not integrated into the mature virus. In the present patent application, the expression "M protein" designates the matrix protein found major in the complex virus, that is to say M1 protein, which may or may not be mixed with other proteins or core fractions.

M protein, which may constitute the additive to the vaccine according to the invention, may be prepared according to known techniques of protein separation and purification; for example, a method similar to that described by RUIGROK et al., Virology, 173, 311–316 (1989).

This process mainly consists in:

treating a core suspension with a surfactant, for example a nonionic surfactant, at a sufficiently high concentration and at a sufficiently acid pH to favour separation of proteins M and NP in the following stage.

subjecting the resultant solution to centrifugation at a speed sufficient for protein Np and any residual core particles to accumulate in the centrifugation pellet while M protein remains in the supernatant.

separating the centrifugation pellet and collecting the supernatant, and concentrating the supernatant if desired, in order to obtain a core fraction solution constituting an additive for a vaccine composition according to the invention.

The nonionic surfactant used is for example a polyoxyethylenated alkyl-phenol- such as Triton X 100 (Rohm & Haas), a polyoxyethylenated fatty alcohol such as Brij 36 T (Sigma) or an alkyl-oside such as octyl beta-D glucopyranoside (or octylglucoside, commercialized by Sigma).

The acid pH favouring separation of proteins M and NP during centrifugation is for example a pH of about 4.8. Centriguation takes place at 85,000 g for 90 minutes, for example.

The final concentration stage of the supernatant may be by ultrafiltration, using for example a membrane having a cut-off threshold of 10,000 Dalton. The concentration factor, for example around 10–20, is obviously chosen in order for the additive to be present in effective amount in a volume compatible with its administration as a vaccine. If necessary, the detergent may be eliminated, for example by dialysis.

The resulting, possibly concentrated supernatant may be used as an additive, in sufficient quantity to obtain an improvement in the vaccination. The quantity of this additive may be assessed for example by reference to the quantity of M protein contained therein.

Detection and dosage of M protein may be carried out for example using specific antibodies, according to classical immunology techniques, such as an ELISA test, as will be detailed below.

The core fractions may also be lipid-free core fractions which may be obtained by gentle treatment of the virus by at least one surfactant, generally used at weak concentration, for example nonionic surfactants such as those commercialized under the name NONIDET P40 or TRITON X100, or certain cationic surfactants such as hexadecyl trimethyl ammonium bromide. Suitable concentrations may be determined in each case by routine experiments; they are concentrations which allow the core to subsist in particle form; see for example Bachmayer, article op. cit. and Rigg et al., J. Gen. Virol, 70, 2097–2109 (1989).

The lipid-free cores are then purified according to usual methods, notably by centrifugation.

When the vaccine additive according to the invention is in the form of core particles, these may be core particles obtained through the action of bromelain (or analogous), and/or lipid-free core particles. In both cases, they are particles virtually free of hemagglutinin and of neuraminidase.

The vaccine composition of the invention may be administered to humans or animals likely to suffer from influenza, notably equine, swine and avian species. The doses of the composition to be administered are the usual ones for this type of vaccine, and may if necessary to determined for animals in each case by routine experiments.

For example, in humans, the unit doses for the first constituent (conventional vaccine) are generally defined by their content of hemagglutinin. For each of the three types of vaccine (vaccine with complete virion, sub-unit vaccine and split vaccine) they generally correspond to 1–20 µg, and particularly 5–20 µg, for example 10–15 µg of hemagglutinin of each of the strains of which they are composed.

These quantities of hemagglutinin may be measured according to the radial immunodiffusion method described by Wool & Coll., Journal of Biological Standardization, 5, 237-247 (1977).

The quantity of additive, in the vaccine composition of the invention, is a predetermined quantity sufficient to cause a statistically significant improvement in the efficiency of the vaccination in the animal species concerned.

The quantity of additive to be used with a unit dose of vaccine is for example a quantity sufficient to cause a statistical improvement of at least 5%, particularly at least 10%, in vaccination efficiency, assessed over at least one recognised ctiterion of vaccination efficiency. The efficiency of the vaccination may be determined for example by epidemiological studies of a population vaccinated with a conventional vaccine, a population vaccinated with the conventional vaccine and the additive, and possibly a non-vaccinated population. The criteria chosen for assessment of vaccination efficiency are those commonly used by those specialized in this field and particularly:

the proportion of vaccinated individuals suffering from an influenza affection, compared to the total number of individuals vaccinated, in a region where an influenza epidemic has indeed develope;

or the severity or duration of the influenza illness, or the number, severity or duration of the illness complications, or protection against a virus subtype other than the subtype(s) used in the preparation of the components (conventional vaccine and additive) of the vaccine, or else the improvement of the effectiveness of the vaccine may be evaluated through a statistically significant enhancement of the immune response, as assessed by the pourcentage of sero-converted subjects, by the amount of antibodies directed against the influenza virus or components thereof, or by tests measuring the immunocompetent cell response to the influenza virus infection.

With certain animals species, particularly laboratory animals or with volunteers, it is also possible to determine the efficiency of a vaccination by using experimental infection.

Unit doses for the second constituent (additive) may generally contain (particularly for humans) 1–100 µg (particularly 2–100 µg, or 5–100 µg) and notably 2–50 µg, for example 5–30 µg, of core particles, or an equivalent quantity of the core fraction used (that is to say, a quantity corresponding to the quantity of the said fraction contained in the said quantity of core particles, or else a quantity of the said fraction having the same activity in the vaccine composition as the said quantity of core particles).

The quantities of core indicated are expressed in quantities of complete proteins measured for example according to the Bradford method mentioned in the experimental section below.

Measurement of the core quantities may be made by separation of the particles according to their density and comparison with a standard core solution.

An analogous method may be used for lipid-free core particles which, contrary to core particles obtained by bromelain treatment, have a higher density than that of the virion.

When the additive is at least one M protein, or a core fraction containing M protein, the unit dose of vaccine composition preferably contains at least 3–5 µg, and particularly at least 7–10 µg of added M protein (that is to say in addition to the free M protein possibly already present in the conventional vaccine, notably when it is a split vaccine). The quantities of M protein indicated are assessed notably by an immunological test according to the ELISA technique. The amounts of M protein as obtained by ELISA are determined by comparison with a purified M protein standard, which is itself quantified, e.g. with bicinchonic acid. One may also proceed by comparison with the M protein content of a purified influenza virus, subjected to a detergent treatment, by assuming that the M protein represents 50% by weight of the total proteins in the virus. The ELISA tests are carried out on tested preparations or on control preparations of M protein of virus, in a solution containing for example 0.1% sodium dodecyl sulfate (SDS). The total proteins are dosed for example by any suitable method, such as the Bradford method mentioned in the experimental section.

It is known that vaccines with complete virions, and sub-unit vaccines are virtually free from free M protein (that is to say, outside the core or virus particles). Conventional split vaccines contain certain quantities of M protein, these quantities being variable and depending mainly on the preparation technique used.

Thus, it is easy to determine the quantities of M protein which have been added to a given vaccine composition, by knowledge of the preparation technique used, and thus of the quantities of free M protein normally present in the vaccine composition obtained by the said technique.

Furthermore, experiments have shown that the added M protein has a density (as measured e.g. in saccharose gradient) which is generally different from that of the M protein already present in the split vaccine composition.

The composition of the invention may be administered subcutaneously, intramuscularly, nasally, orally, or as an aerosol.

It may be administered in association with other vaccines and/or additives.

The composition may also be used for booster injections, for example 1 to 3 months after the first vaccination.

Another object of the invention is the use of an additive constituted by core of at least one influenza virus or by a fraction of core of at least one influenza virus, in the preparation of a vaccine composition against influenza comprising a conventional influenza vaccine.

The invention particularly concerns use of a second constituent (additive) containing core, or a purified core fraction, of at least one influenza virus, in the preparation of a vaccine composition against influenza containing a first constituent corresponding to a conventional influenza vaccine, it being possible for the said first and second constituents to be present in one and the same container, or in separate containers, as aforementioned.

The following examples illustrate the invention but do not limit it.

BRIEF DESCRIPTION OF FIGURES

FIG. 2 shows a comparison of influenza vaccine profiles (one dose) before (a) and after (b) addition of 10 µg viral core (FIG. 2 is comprised of six graphs: graph 1a, FIG. 2.1a shows vaccine profile before addition of vaccine core, with vaccine being complete virions; graph 1b, FIG. 2.1b shows vaccine profile after addition of vaccine core, with vaccine being complete virions; graphs 2a and 3a, FIGS. 2.2a and 2.3a sow vaccine profile before addition of vaccine core, with vaccines being split vaccines; and graphs 2b and 2b, FIGS. 2.2b and 2.3b show vaccine profile after addition of vaccine core, with the vaccines being split vaccines).

EXAMPLE 1

Obtaining Purified Viral Core

Figure 1:
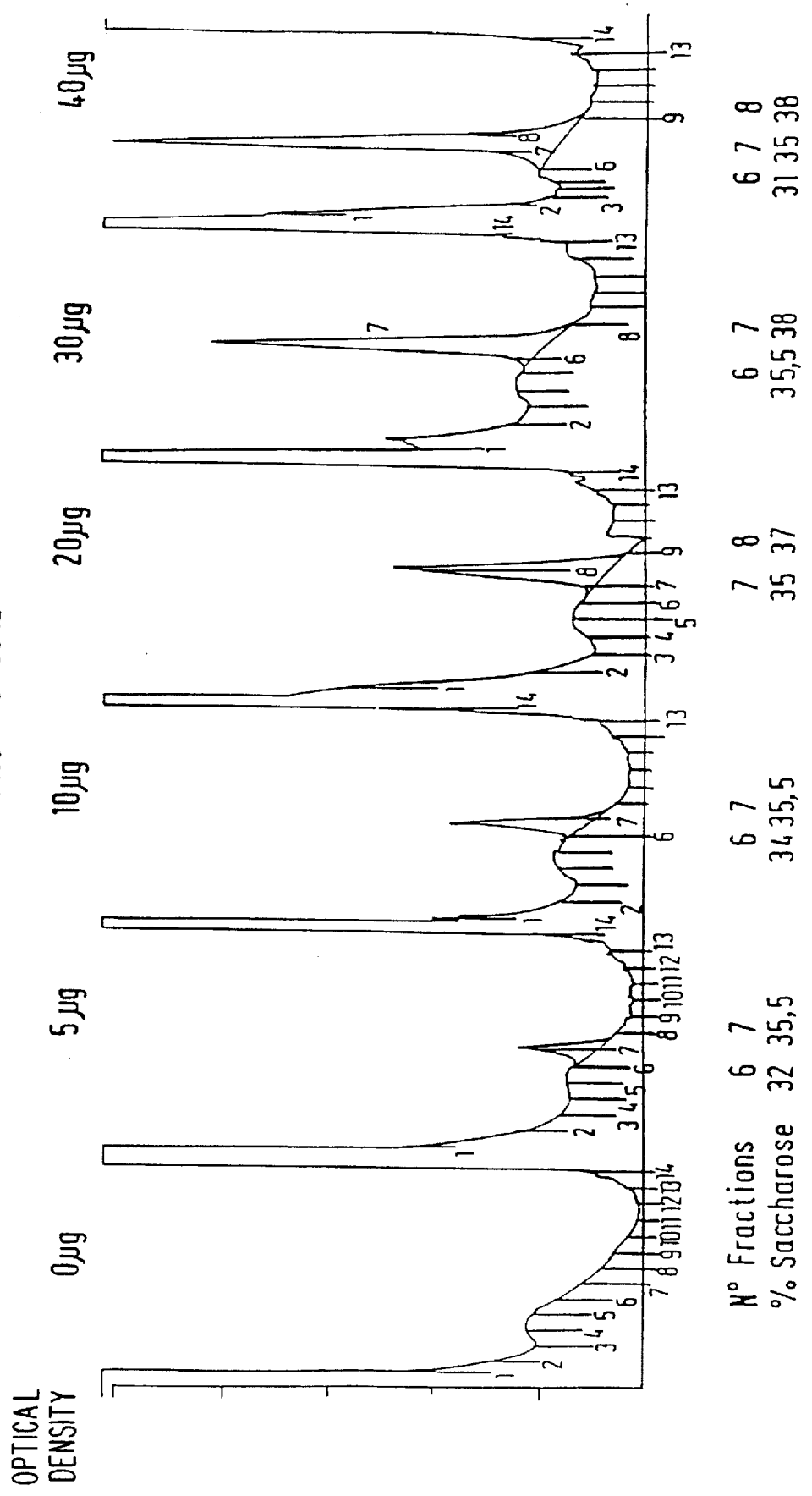
FIG. 1 shows the results of density analysis of a core solution.

The reassortant strain of influenza virus NIB16 (A/H1N1) was used: said strain originates from mating wild strains A/Taiwan/1/86 (A/H1N1) and reassortant X31 (A/H3N2), the latter being obtained by mating strain A/Aichi/2/68 with the A/Porto-Rico/8/34 (A/H1N1) virus.

Strain NIB16 may be obtained form the NIBSC.

The viral suspensions were prepared by multiplication on chick embryonated eggs, concentration by ultrafiltration and purification on saccharose gradient as described in French patent application n° 2 201 079.

To extract the core, the purified virus, suspended in phosphate buffer pH 7.4 (PBS buffer), is subjected to two or three successive treatments with bromelain (Sigma) at 37° C. in 0.1M tris buffer pH 7.5, 1 mM EDTA, 50 mM beta-mercaptoethanol. For the first treatment with the protease, the viral suspension, adjusted to contain 2 mg of proteins per ml of buffer solution, is used, and 1 mg/ml of bromelain is added. After 2 hours' incubation at 37° C. and dilution with an aqueous solution of 0.1M NaCl, the preparation is subjected to separation by ultra-centrifugation at 120,000 g, for 90 min, at +4° C. For the second and if necessary the third treatment, incubation is carried out by using bromelain at 2 mg/ml (final concentration) for 16 hours. The centrifugation treatments are the same as for the first treatment and the pellets are re-suspended in PBS buffer.

The core solution obtained is subjected to purification by isopycnic ultra-centrifugation on a 20–60% (w/w) linear saccharose gradient in PBS buffer at 100,000 g, for 16 hours, at +4° C. The fractions containing viral core are diluted by one third with PBS buffer, then subjected to ultra-centrifugation at 120,000 g for 90 minutes, at +4° C. The centrifugation pellet is recovered by PBS buffer pH 7.4, to which 0.01% sodium azide has been added. The solution may be preserved by freezing at minus 20° C.

The purified core preparation thus obtained presents the following characteristics:

the proportion of hemagglutinin is a maximum of 4% compared to the total protein, this proportion being measured by polyacrylamide gel electrophoresis (Laemmli, Nature 227, 680–685, 1970) or by the ELIZA technique;

hemagglutinating activity is less than 0.01% that of the original virus (measurement by hemagglutination according to the method described by Palmer et al., Advanced Laboratory Technicals for Immunological Diagnostic, U.S. Dept. Hlth Ed. Welfare, PHS, Atlanta, Immunology ser. n° 6, Procedural Guide Part 2, hemagglutination inhibition Test, 1975, 25–62).

the final vaccine is prepared by diluting in PBS buffer, as indicated in example 2 below.

EXAMPLE 2

Preparation of the Vaccine and Pharmacological Study

As first constituent of the vaccine composition an inactivated monovalent split vaccine, obtained with the NIB16 strain, was used.

The hemagglutinin of NIB16 is analogous to that of the A/Singapore/6/86 (A/H1N1) strain.

This split vaccine was obtained by treating the virus with the mixture of Polysorbate 80 and ether, according to the method described in French patent 2 201 079 (example 1).

The second constituent (core) was obtained according to the procedure described in example 1 above.

The monovalent vaccine and the core were diluted and mixed in PBS buffer to provide the combinations and doses indicated in tables 1 and 2 below, in a total volume of 0.5 ml. The composition thus obtained was injected subcutaneously into six-week-old OF1 mice (IFFA-CREDO France).

The doses of split vaccine and core used are expressed in µg of total proteins determined by colorimetry, by comparison with a standard solution of bovine serum albumine, according to the method described by Bradford (Anal. Biochem. 1976, 72, 248–354), using the Bio-rad Kit.

One month after vaccination, the mice were infected with the A/Wilson Smith/33 (A/H1N1) strain, obtained from the World Influenza Centre in London. This strain was chosen for the infection challenge since it is lethal for non-immunized mice. It was administered nasally, at the rate of 20 LD50 doses in 30 µl per mouse under anaesthetic. The mice were then observed daily for three weeks.

The results concerning survival for the different experimental groups were recorded in tables 1 and 2. In the experiments in table 1, no control mouse (unvaccinated) survived. The viral core administered alone had at best a limited protective effect (10–20%), and the split vaccine injected alone only protected 30 to 50% of the mice. It may be seen that several of the split and core vaccine combinations gave synergic protection at concentrations higher than 3 µg of split vaccine associated with 90 µg of core, or else, 10 µg of split vaccine associated with 10 µg of core.

The increased survival obtained by associating split vaccine and core is statically significant. The results were subjected to variance analysis (FISCHER-SNEDECOR test F), which showed that the addition of core has a statistically significant synergic effect (p=0.027) on survival of the vaccinated mice.

The experiment was repeated, reducing the range of core quantities tested in associated with the split vaccine. The results are presented in table 2. From the results in table 2, it may be seen that the addition of 3 µg of core or more to the vaccine systematically increases the percentage of mice surviving the test (highly significant protection synergy: p test F=0.009).

TABLE 1

| Split | Surviving mice/Tested mice after immunisation, with, per mouse: | | | |
|---|---|---|---|---|
| | with added core (µg): | | | |
| Vaccine (µg) | 0 | 10 | 30 | 90 |
| 0 (only PBS) | 0/10 | 1/10 | 2/10 | 2/10 |
| 3 | 3/10 | 2/10 | 3/10 | 8/10 |
| 10 | 4/10 | 7/9 | 10/10 | 7/10 |
| 30 | 5/10 | 10/10 | 7/10 | 8/10 |

TABLE 2

| Split | Surviving mice/Tested mice after immunisation, with, per mouse: | | |
|---|---|---|---|
| | with added core (µg): | | |
| Vaccine (µg) | 0 | 3 | 10 |
| 0 (only PBS) | 0/10 | 0/10 | 1/10 |
| 3 | 2/10 | 8/10 | 10/10 |
| 10 | 6/10 | 10/10 | 10/10 |

EXAMPLE 3

Detection and Quantification of the Influenza Virus Core

The influenza vaccines of the invention are likely to contain lipid-free or complete influenza core particles and complete virions or protein sub-units in variable proportions depending on their method of preparation.

The method chosen to dose the core uses the difference in density of these elements, shown by isopycnic centrifugation in linear SUCROSE gradient (Brand & Skehel, article op. cit.).

With this aim, the samples to be analysed were placed in ultra-centrifugation tubes on the surface of a preformed saccharose gradient. In the present case, 14 ml tubes with a 12 ml 20–60% gradient (w/w in PBS) were used. The vaccine dose placed in the tubes was 1 ml in volume.

The samples were then subjected to ultracentrifugation for 16 hours at 100,000 g (at +4° C.), then the contents of the tubes were fractioned from the surface to the bottom in 14 aliquotes. During fractioning, optical density was measured continuously at 254 mm.

A diagram in which each peak corresponded to a population of particles of determined density was obtained. The apparatus makes it possible to pinpoint the correspondence between the position of a peak on the graph and the fraction in which it may be found. Measurement with the Abbe refractormeter shows the saccharose percentage for each fraction, from which conversion tables (Handbook of Chemistry and Physics, 68th. Edition, Ed. R. C. Weast, GRC Press Inc.) give the apparent density of the particles. Characteristically, the density of the viral core (obtained according to the procedure of example 1) is 1.15–1.16 g/cm$^3$ and that of the virus is 1.19–1.20 g/cm$^3$, this corresponds to saccharose concentrations of 35–37% and 42–44% respectively.

The results of the density analysis of a standard core solution are shown in FIG. 1.

In the graphs of the density analysis of a standard core solution are shown in FIG. 1.

In the graphs of FIG. 1 the numbers of the fractions are shown in absciss (and the corresponding saccharose concentrations) and the optical density (DO) in arbitrary units in ordinate. The recording conditions (ISCO material) were the following: detection wavelength 254 nm, sensitivity 0.2 of DO (full scale), rate of collection: 3 ml/cm.

The graphs shown in FIG. 1 were obtained by testing increasing quantities of core in solution in the PBS buffer. It was noticed that the surface delimitated by the peaks was proportional to the quantity of core. A correlation may be established which enables the method to be used for dosage.

In order to confirm that the peak observed for a saccharose concentration of 35–37% is viral core, polyacrylamide gel electrophoresis (Laemmli, see above) may be used, after denaturing treatment of the sample by SDS at 2%, at 90° C. for 3 minutes, which shows the presence of core proteins NP and M after coloration with silver.

In FIG. 2, the diagrams obtained with 3 different vaccines are shown: a vaccine with complete virions, commercialized under the trade name Vaccin Grippal Ronchèse (VGR), and two split vaccines obtained with different techniques and commercialized under the trade names VAXIGRIP and MUTAGRIP, these diagrams being established according to the same principles and in the same recording conditions as those described concerning FIG. 1. FIG. 2 allows comparison of influenza vaccine profiles (one dose) before (a) and after (b) addition of 10 µg of viral core. In FIG. 2, graph 1 corresponds to the vaccine with complete virions, and graphs 2 and 3 to the split vaccines (Vaxigrip and Mutagrip respectively). The profiles vary from one vaccine to another but none of them have a content of core.

The addition of core (10 µg/dose) (graphs 1b, 2b, 3b) is clearly identifiable by the appearance of a new peak in the fractions containing saccharose at 36–37%.

EXAMPLE 4

Preparation of a Core Fraction Containing a Matrix Protein (M Protein); Vaccination and Dosage Tests The bibliographical references in this example are to be found at the end of the example.

This fraction is extracted form purified viral core according to a technique adapted from Ruigrok and coll. (1989). The core is suspended in PBS buffer adjusted to pH 4.8 with a 0.25M solution of citric acid. At this stage, a protease inhibitor such as TLCK (Sigma, solution at 1 mg/ml in 50 mM pH5 acetate buffer) may be added, to avoid later degradation of the M protein. The core is then subjected to a detergent treatment by a 10% solution of lubrol (Brij 36T, Sigma) the final concentrations of core, lubrol and where necessary TLCK being respectively brought to 0.1 mg/ml 0.5% and 50 µg/ml, by addition of PBS buffer adjusted to pH 4.8 with 1.24N hydrochloric acid. The mixture is homogenised by gentle stirring at room temperature for one minute, then subjected to ultra-centrifugation at 85,000 g for 90 min. at +4° C. The centrifugation pellets, containing nucleoprotein (NP) are once more suspended in PBS Buffer pH 7.4, while the supernatant, containing the M protein, is concentrated 10–20 times by ultrafiltration (Amicon cell, membrane with cut-off threshold of 10,000 Daltons). The proteins are stocked at –20° C.

They are dosed with bicinchonic acid (Smith, Krohn et al., 1985) using the Pierce Micro BCA Kit.

Their purity is routinely checked by 12.5% polyacrylamide gel electrophoresis followed by coloration with Coomassie blue (Phast System, Pharmacia). No contamination was visible as regarded the matrix protein, which indicates a purity of at least 90%.

Dosage of M Protein by ELISA

Principle:

The technique used was a non-competitive ELIZA sandwich test adapted from Bucher, Kharitonenkov et al., (1987), Donofrio, Coonrod et al., (1986), and Hjerten, Sparrman et al., (1988). It consisted in capturing the M protein in the samples to be dosed (for example: influenza virus, vaccine, core, purified proteins) using specific anti-M immunoglobulins adsorbed on microtitration plates; the presence of the M protein was then assessed using a succession of stages which led to a colorimetrical reaction proportional to the quantity of antigen present.

Immunological reagents used:

Total anti-influenza virus M protein immunoglobulins: these specific immunoglobulins were obtained form serum from rabbits hyperimmunized by 3 injections respectively of 100, 75 and 75 µg of M protein prepared as previously described; these injections were made intra-muscularly at monthly intervals in presence of Freund's adjuvant (complete adjuvant for the first injection and incomplete for the subsequent ones). The total immunoglobulins were then precipitated with ammonium sulphate at 35% saturation.

Commercial Monoclonal murine anti-M antibody (Serotec)

Anti (mouse immunoglobulin) goat immunoglobulins, labelled with peroxidase (Jackson ImmunoResearch).

Solutions:

Dilution buffer constituted of PBS pH 7.2 with 0.05% tween 20 and 5% of skimmed powdered milk (Régilait) added.

Washing solution for wells constituted of PBS buffer plus 0.05% of tween 20.

Method:

It is carried out in microtitration plates (Nunc). Each reagent is added under a volume of 100 µl per well: after the saturation stage and up to that of revelation, the plates systematically undergo 4 successive rincings with the washing solution.

The total anti-M protein rabbit immunoglobulins are deposited at a concentration of 1 µg/ml in sodium carbonate 50 mM pH 9.6 buffer and are adsorbed for one night at +4° C.

A well saturation stage is then carried out for 1 h at 37° C. with the help of the dilution buffer.

The samples to be dosed are then placed in the form of rate 2 dilutions in the dilution buffer to which 0.1% of SDS has been added.

After 2 hours' contact at 37° C., the mouse monoclonal antibody specific to the M protein, diluted at 1/1,000 in the dilution buffer containing 0.1% SDS, is added and incubated for 1 h at 37° C.

Binding of the monoclonal anti-M antibody on the protein is evidenced by addition of the anti-mouse immunoglobulin antibodies labelled with peroxidase and diluted at 1/1,000 in the dilution buffer.

After 1h at 37° C. and after a final series of plate washing, the reaction is revealed by addition of the 20 mM citrate buffer, pH 5.6, containing sodium perborate, substrate of the peroxidase (Sigma), with added oPD (orthophenylenediamine dihydrochloride, Sigma) used at a concentration of 0.4 mg/ml. The reaction is halted after incubation for 20 min at room temperature by adding 50 µl of 4N sulphuric acid.

The result is read by using an ELIZA plate reader (MR 5.000 Dynatech) which measures absorbency of the ractional medium in the wells at a wavelength of 490 nm.

Protection Tests on Mice

Groups of six-week-old BALB/c mice (from IFFA-Credo, France) were immunized with preparations of Vaxigrip (monovalent A/H1N1 NIB16), with viral protein M, or by associations of Vaxigrip and M protein (see doses used in the result tables). The various preparations were administered subcutaneously under 0.5 ml without adjuvant and in a single injection. The mice were tested 4 to 5 weeks after immunization with 5 50% lethal doses (LD50) of the A/H1N1 A/WS/33 strain inoculated under 30 µl intranasally, under deep anaesthesia of the animals by a mixture of ketamine-Xylazine. The results are presented as the survival table of the mice three weeks after infection challenge.

The two tables presented correspond to two series of experiments carried out with the same M and NIB16 virus core protein preparations. They show that the association of Vaxigrip (monovalent NIB16) and matrix protein preparation improves the protection.

The doses of vaccine, core and protein are expressed in µg of total proteins determined for the vaccine and the core by Bradford's technique (1976, op. cit. in patent), and for M protein by dosage with bicinchonic acid (Smith, Khron et al. 1985, op. cit.).

TABLE 3

| No of surviving mice/No of tested mice (10 unless otherwise stated) | | | |
|---|---|---|---|
| Vaccine | NIB16 M protein (µg) | | |
| NIB16 (µg) | 0 | 5 | 15 |
| 0 | 0 | 1/9 | 1 |
| 10 | 0 | 7 | 7/9 |

TABLE 4

| No of surviving mice/10 tested mice | | |
|---|---|---|
| NIB16 vaccine | NIB16 M protein | |
| (µg) | 0 | 5 µg |
| 0 | 1 | 0 |
| 10 | 2 | 9 |

The mice may also be immunized using vaccine preparations with complete virions. The table below presents survival of BALB/c mice immunized at age 6 weeks with trivalent VGR vaccine preparations with complete virions (Vaccin Grippal Ronchèse from the 1990–91 season). The trivalent vaccine dose used was about 5 µg hemagglutinine of NIB16 virus per mouse; it was quantified by radial immunodiffusion according to the technique of Wood & coll., op. cit., and corresponds to the quantity present in 10 µg of total proteins of monovalent Vaxigrip NIB16 previously used.

The results show that the improvement effect in protection by addition of M protein preparation may also be observed with a complete virus vaccine:

TABLE 5

| No of surviving mice/10 mice tested | | | |
|---|---|---|---|
| Complete virion VGR vaccine | M Protein NIB16 (µg) | | |
| (µg HA NIB16) | 0 | 5 | 15 |
| 0 | 0 | 0 | 0 |
| 5 | 2 | 4 | 7 |

In the same way as before, the BALB/c mice were immunized using sub-unit vaccine preparations, such as the DUPHAR vaccine (Influvac sub-unit); this is obtained after treatment of the virus by hexadecyl trimethyl ammonium bromide (Jennings, Smith et al. 1984; Bachmayer, 1975) and purification of the HA and NA glycoproteins by ultracentrifugation on saccharose gradient.

This sub-unit vaccine may be associated with core particles or a core fraction containing M protein using equivalent doses to those in the previous tests, i.e. for the monovalent or trivalent vaccine: the equivalent of 5 µg of HA of virus NIB16 assessed by radial immunodiffusion; for the M protein: 5, 15 or 30 µg of protein dosed by the bicinchonic acid method, and for the core, 30 µg of total protein dosed by Bradford's method.

Bibliographical References

Bachmayer, H. (1975). "Selective solubilization of hemagglutinin and neuraminidase from influenza viruses." *Intervirology*, 5, 260–272.

Bradford, M. M. (1976). "A rapid and sensitive method for the quantitation of microgram quantities of proteins utilizing the principle of protein-dye binding." *Anal Biochem.* 72, 248–254.

Bucher, D. J., Kharitonenkov, I. G., Wajeed-Khan, M., Palo, A., Holloway, D. and Mikhail, A. (1987). "Detection of influenza viruses through selective adsorption and detection of the M protein antigen." *J. of Immunol. Methods*, 96, 77–85.

Donofrio, J. C., Coonrod, J. D., Karathanasis, K. and Coelingh, K. V. W. (1986). "Electroelution for purification of influenza A matrix protein for use in immunoassay." *J. of Immunol. Methods*, 13, 107–120.

Hjerten, S., Sparrman, M. and Liao, J. (1988). "Purification of membrane proteins in SDS and subsequent renaturation." *Biochim. Biophys. Acta.* 939, 476–484.

Jennings, R., Smith, T. L., Spencer, R. C., Mellersh, A. M., Edey, D., Fenton, P., et al (1984). "Inactivated influenza virus vaccines in man: a comparative study of subunit and split vaccines using two methods for assessment of antibody responses." *Vaccine*, 2, 75–080.

Ruigrok, R. W. H., Calder, L. J. and Wharton, S. T. A. (1989). "Electron Microscopy of the Influenza Virus Submembranal Structure." *Virology*, 173, 311–316.

Smith, P. K. Krohn, R. I., Hermanson, G. T., Mallia, A. K., Gartner, F. H., Provenzano, M. D., et al (1985). "Measurement of protein using bicinchonic acid." *Anal. Biochem.*, 150, 76–85.

EXAMPLE 5

Improvement of Protection against a Sub Type of the Influenza Virus by use of a Different Sub-Type vaccine Containing Core Groups of OF1 male mice aged 6 weeks were treated with preparations of monovalent Vaxigrip A/H3N2×97, A/H3N2×97 virus core, or with associations of Vaxigrip and core. The different preparations were administered subcutaneously under a volume of 0.5 ml, without adjuvants and in a single injection. The mice were tested 5 weeks after immunization with a dose corresponding to 20 50% lethal doses (LD50) of the A/H1N1 A/WS/33 strain inoculated intra-nasally under a volume of 30 μl, under deep anaesthesia of the animals by a mixture of ketamine-Xylazine.

The results were summed up in the following table:

TABLE 6

| Vaccine X97 (μg) | core X97 added (μg) | | | |
|---|---|---|---|---|
| | 0 | 3 | 10 | 30 |
| 0 | 0/9 | 0/9 | 0 | 0 |
| 8 | 0 | 0 | 0 | 0/9 |
| 10 | 1 | 3 | 3 | 1 |
| 30 | 0 | 1 | 4 | 7 |

No surviving mice/no tested mice (10 unless otherwise stated)

as expected, vaccine A/H3N2 X97 does not afford protection against an infection challenge with virus A/H1N1. A surprising effect of protection synergy is observed however when the vaccine is associated with core.

We claim:

1. In a vaccine composition which comprises an anti-influenza vaccine selected from the group consisting of a complete virion vaccine, a sub-unit vaccine, and a split vaccine, wherein the improvement comprises having an additive selected from the group consisting of: M protein from at least one influenza virus strain; an isolated influenza virus core particle including M protein from at least one influenza virus strain; and an isolated portion, including M protein, of an influenza virus core particle, from at least one influenza virus strain.

2. A method for inducing an immunological response in a host comprising inoculating said host with the vaccine composition according to claim 1.

3. A vaccine composition according to claim 1, wherein said anti-influenza vaccine is a complete virion vaccine.

4. A vaccine composition according to claim 1, wherein said anti-influenza vaccine is a split vaccine.

5. A vaccine composition according to claim 1, wherein said anti-influenza vaccine is a sub-unit vaccine.

6. A vaccine composition according to claim 1 wherein it is presented in the form of a unit dose containing an immunologically effective amount of the additive sufficient to effect enhancement of the anti-influenza vaccine.

7. A vaccine composition according to claim 6 wherein it contains as the additive at least 3–5 μg of M protein.

8. A vaccine composition according to claim 6 wherein it contains as the additive at least 7–μg of M protein.

9. A vaccine composition according to claim 6 wherein its anti-influenza vaccine component contains from 1 to 20 μg of hemagglutinin of each of the strains of which it is composed.

10. The vaccine composition of claim 1 wherein the additive comprises isolated M protein.

11. The vaccine composition of claim 1 wherein the additive comprises an isolated portion of an influenza virus core particle.

12. The vaccine composition of claim 1 wherein the additive comprises an isolated influenza virus core particle.

13. A method for inducing an immunological response in a host comprising inoculating the host with the vaccine composition of claim 10.

14. A method for inducing an immunological response in a host comprising inoculating the host with the vaccine composition of claim 11.

15. A method for inducing an immunological response in a host comprising inoculating the host with the vaccine composition of claim 12.

16. A vaccine composition according to claim 10, wherein said anti-influenza vaccine is a split vaccine.

17. A vaccine composition according to claim 10, wherein said anti-influenza vaccine is a sub-unit vaccine.

18. A vaccine composition according to claim 10, wherein said anti-influenza vaccine is a complete virion vaccine.

19. A vaccine composition according to claim 11, wherein said anti-influenza vaccine is a split vaccine.

20. A vaccine composition according to claim 11, wherein said anti-influenza vaccine is a sub-unit vaccine.

21. A vaccine composition according to claim 11, wherein said anti-influenza vaccine is a complete virion vaccine.

22. A vaccine composition according to claim 12, wherein said anti-influenza vaccine is a split vaccine.

23. A vaccine composition according to claim 12, wherein said anti-influenza vaccine is a sub-unit vaccine.

24. A vaccine composition according to claim 12, wherein said anti-influenza vaccine is a complete virion vaccine.

25. A vaccine according to claim 10, wherein it is presented in the form of a unit does containing an immunologically effective amount of the additive sufficient to effect enhancement of the anti-influenza vaccine.

26. A vaccine according to claim 11, wherein it is presented in the form of a unit does containing an immunologically effective amount of the additive sufficient to effect enhancement of the anti-influenza vaccine.

27. A vaccine according to claim 12, wherein it is presented in the form of a unit dose containing an immunologically effective amount of the additive sufficient to effect enhancement of the anti-influenza vaccine.

28. A vaccine composition according to claim 25 wherein it contains as the additive at least 3–5 µg of M protein.

29. A vaccine composition according to claim 26 wherein it contains as the additive at least 3–5 µg of M protein.

30. A vaccine composition according to claim 27 wherein it contains as the additive at least 3–5 µg of M protein.

31. A vaccine composition according to claim 25 wherein in contains as the additive at least 7–10 µg of M protein.

32. A vaccine composition according to claim 26 wherein it contains as the additive at least 7–10 µg of M protein.

33. A vaccine composition according to claim 27 wherein it contains as the additive at least 7–10 µg of M protein.

34. A vaccine composition according to claim 25 wherein its anti-influenza vaccine component contains form 1 to 20 µg of hemagglutinin of each of the strains of which it is composed.

35. A vaccine composition according to claim 26 wherein its anti-influenza vaccine component contains from 1 to 20 µg of hemagglutinin of each of the strains of which it is composed.

36. A vaccine composition according to claim 27 wherein its anti-influenza vaccine component contains from 1 to 20 µg of hemagglutinin of each of the strains of which it is composed.

37. An anti-influenza vaccine kit comprising as a first component at least one anti-influenza vaccine selected from the group consisting of a complete virion vaccine, a sub-unit vaccine, and a split vaccine, and, a second component selected from the group consisting of: M protein from at least one influenza virus strain; an isolated influenza virus core particle including M protein from at least one influenza virus strain; and an isolated portion, including M protein, of an influenza virus core particle, from at least one influenza virus strain.

38. The vaccine kit according to claim 37, wherein said first component and the second component are present in the same container.

39. The vaccine kit according to claim 37, wherein said first component and the second component are present in separate containers, placed in the same wrapping.

40. The kit of claim 37 wherein the second component comprises isolated M protein.

41. The kit of claim 37 wherein the second component comprises an isolated portion of an influenza virus core particle.

42. The kit of claim 37 wherein the second component comprises an isolated influenza virus core particle.

43. A vaccine kit according to claim 40, wherein said first component and the second component are present in the same container.

44. A vaccine kit according to claim 40, wherein said first component and the second component are present in separate containers, placed in the same wrapping.

45. A vaccine kit according to claim 41, wherein said first component and the second component are present in the same container.

46. A vaccine kit according to claim 41, wherein said first component and the second component are present in separate container, placed in the same wrapping.

47. A vaccine kit according to claim 42, wherein said first component and the second component are present in the same container.

48. A vaccine kit according to claim 42, wherein said first component and the second component are present in separate containers, placed in the same wrapping.

49. In a vaccine composition which comprises an anti-influenza vaccine selected from the group consisting of a complete virion vaccine, a sub-unit vaccine, and a split vaccine, wherein the improvement comprises having an additive which includes M protein from at least one influenza virus strain wherein the additive is obtained by a process consisting essentially of:

treating a core suspension with a surfactant, at a sufficiently high concentration and at a sufficiently acid pH to favor separation of proteins M and NP in the following stage to form a resultant solution, subjecting the resultant solution to centrifugation to form a centrifugation pellet and a supernatant, said centrifugation being at a speed sufficient for protein NP and any residual core particles to accumulate in the centrifugation pellet while M protein remains in the supernatant, and separating the centrifugation pellet and collecting the supernatant.

50. The vaccine composition of claim 49 wherein the process for obtaining the additive further comprises concentrating the supernatant.

51. A method for inducing an immunological response in a host comprising inoculating said host with the vaccine composition according to claim 49.

52. A vaccine composition according to claim 49 wherein the surfactant is a nonionic surfactant.

53. A method for inducing an immunological response in a host comprising inoculating said host with the vaccine composition according to claim 50.

54. The vaccine of claim 52 wherein the nonionic surfactant is selected from the group consisting of polyoxyethylenated alkylphenols, polyxyethylenated fatty alcohols and alkyl-osides.

55. A method for inducing an immunological response in a host comprising inoculating said host with the vaccine composition according to claim 54.

56. A method for inducing an immunological response in a host comprising inoculating said host with the vaccine composition according to claim 52.

* * * * *

UNITED STATES PATENT AND TRADEMARK OFFICE
CERTIFICATE OF CORRECTION

PATENT NO. : 5,741,493
DATED : April 21, 1998
INVENTOR(S) : Moste-Deshairs et al.

It is certified that error appears in the above-identified patent and that said Letters Patent is hereby corrected as shown below:

Column 15, line 18
Claim 34, Line 2, change "form" to --from--.
Column 16, line 6
Claim 46, Line 3, change "container" to --containers--.

Signed and Sealed this

Twenty-seventh Day of October, 1998

Attest:

BRUCE LEHMAN

*Attesting Officer*  *Commissioner of Patents and Trademarks*